US007888083B2

(12) United States Patent
Blacker et al.

(10) Patent No.: US 7,888,083 B2
(45) Date of Patent: Feb. 15, 2011

(54) PROCESS FOR THE PREPARATION OF DIHYDROXY ESTERS AND DERIVATIVES THEREOF

(75) Inventors: Andrew John Blacker, Huddersfield (GB); Christopher David Reeve, Billingham (GB); Robert Antony Holt, Billingham (GB)

(73) Assignee: AstraZeneca UK Limited, London (GB)

( * ) Notice: Subject to any disclaimer, the term of this patent is extended or adjusted under 35 U.S.C. 154(b) by 0 days.

(21) Appl. No.: 12/768,459

(22) Filed: Apr. 27, 2010

(65) Prior Publication Data
US 2010/0209984 A1 Aug. 19, 2010

Related U.S. Application Data

(60) Division of application No. 12/178,424, filed on Jul. 23, 2008, now Pat. No. 7,732,171, which is a continuation of application No. 11/412,047, filed on Apr. 27, 2006, now Pat. No. 7,416,865, which is a continuation of application No. 10/275,092, filed as application No. PCT/GB01/01915 on May 1, 2001, now Pat. No. 7,157,255.

(30) Foreign Application Priority Data
May 9, 2000 (GB) ................................. 0011120.3

(51) Int. Cl.
C12P 7/62 (2006.01)
C07C 69/66 (2006.01)
C12N 9/14 (2006.01)

(52) U.S. Cl. ........................ 435/135; 435/125; 435/169; 435/183; 435/196; 514/547; 560/186

(58) Field of Classification Search ........................ None
See application file for complete search history.

(56) References Cited

U.S. PATENT DOCUMENTS

| 3,325,466 | A | 6/1967 | Anderson et al. |
| 3,992,432 | A | 11/1976 | Napier et al. |
| 4,248,889 | A | 2/1981 | Oka et al. |
| 5,278,313 | A | 1/1994 | Thottathil et al. |
| 5,457,227 | A | 10/1995 | Thottathil et al. |
| 5,559,030 | A | 9/1996 | Matsuyama et al. |
| 5,594,153 | A | 1/1997 | Thottathil et al. |
| 5,700,670 | A | 12/1997 | Yamagishi et al. |
| 6,001,618 | A | 12/1999 | Kimoto et al. |
| 6,225,099 | B1 | 5/2001 | Hummel et al. |
| 6,278,001 | B1 | 8/2001 | Solladie et al. |
| 6,331,641 | B1 | 12/2001 | Taoka et al. |
| 6,340,767 | B1 | 1/2002 | Nishiyama et al. |
| 6,344,569 | B1 | 2/2002 | Mitsuda et al. |
| 6,472,544 | B1 | 10/2002 | Kizaki et al. |
| 6,784,171 | B2 | 8/2004 | Taylor et al. |
| 6,844,437 | B1 | 1/2005 | Taylor et al. |
| 6,870,059 | B2 | 3/2005 | Kooistra et al. |
| 6,903,225 | B2 | 6/2005 | Kizaki et al. |
| 7,094,594 | B2 | 8/2006 | Nishiyama et al. |
| 7,157,255 | B2 | 1/2007 | Blacker et al. |
| 7,304,156 | B2 | 12/2007 | Matsushita et al. |
| 7,416,865 | B2 | 8/2008 | Blacker et al. |
| 7,442,811 | B2 | 10/2008 | Bakel Van et al. |
| 7,511,140 | B2 | 3/2009 | Horbury et al. |
| 7,524,955 | B2 | 4/2009 | Newton et al. |
| 7,642,363 | B2 | 1/2010 | Kooistra et al. |
| 7,732,171 | B2 * | 6/2010 | Blacker et al. ............... 435/135 |
| 2005/0090674 | A1 | 4/2005 | Hof |
| 2006/0004200 | A1 | 1/2006 | Gudipati et al. |
| 2006/0040898 | A1 | 2/2006 | Puthiaparampil et al. |
| 2006/0293355 | A1 | 12/2006 | Booth et al. |
| 2007/0105882 | A1 | 5/2007 | Black et al. |
| 2007/0255060 | A1 | 11/2007 | Okada et al. |
| 2008/0058520 | A1 | 3/2008 | Matsushita et al. |
| 2008/0188657 | A1 | 8/2008 | Lenger |
| 2008/0207903 | A1 | 8/2008 | Butters et al. |
| 2008/0221323 | A1 | 9/2008 | Crabb et al. |
| 2008/0280336 | A1 | 11/2008 | Blacker et al. |
| 2009/0264654 | A1 | 10/2009 | Newton et al. |
| 2009/0286819 | A1 | 11/2009 | Horbury et al. |

FOREIGN PATENT DOCUMENTS

EP 0 569 998 11/1993

(Continued)

OTHER PUBLICATIONS

Barry et al. (1982) Easy and Efficient Anion Alkylations in Solid-Liquid PTC Conditions, Tetrahedron Lett. 23(51):5407-5408.

(Continued)

*Primary Examiner*—Herbert J. Lilling
(74) *Attorney, Agent, or Firm*—Morgan Lewis & Bockius LLP

(57) ABSTRACT

A process is provided for the preparation of a compound of formula (1)

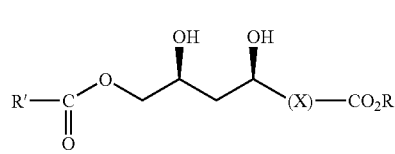

Formula 1 wherein R and R' represent optionally substituted hydrocarbyl groups and X represents a hydrocarbyl linking group. The process comprises either the stereoselective reduction of the keto group in a dihydroxy keto precursor followed by selective esterification of a primary hydroxy, or selective esterification of a primary hydroxy of a dihydroxy keto precursor followed by stereoselective reduction of the keto group.

7 Claims, No Drawings

FOREIGN PATENT DOCUMENTS

| | | |
|---|---|---|
| EP | 0 579 370 | 1/1994 |
| EP | 0 606 899 | 7/1994 |
| EP | 0 737 751 | 10/1996 |
| EP | 0 796 914 | 9/1997 |
| EP | 0 862 646 B1 | 9/1998 |
| EP | 1 024 139 B1 | 8/2000 |
| GB | 885516 | 12/1961 |
| JP | 4-266879 | 9/1992 |
| WO | WO 91/13876 | 9/1991 |
| WO | WO 93/06235 | 4/1993 |
| WO | WO 93/08823 | 5/1993 |
| WO | WO 96/31615 | 10/1996 |
| WO | WO 97/00968 | 1/1997 |
| WO | WO 97/19185 | 5/1997 |
| WO | WO 97/19917 | 6/1997 |
| WO | WO 99/57109 | 11/1999 |
| WO | WO 00/08011 | 2/2000 |
| WO | WO 00/34264 | 6/2000 |
| WO | WO 00/36134 | 6/2000 |
| WO | WO 00/49014 | 8/2000 |
| WO | WO 00/68221 | 11/2000 |
| WO | WO 01/04336 | 1/2001 |
| WO | WO 01/72706 | 10/2001 |
| WO | WO 01/85975 | 11/2001 |
| WO | WO 02/06266 | 1/2002 |
| WO | WO 03/006439 | 1/2003 |
| WO | WO 03/059901 | 7/2003 |
| WO | WO 03/087112 | 10/2003 |
| WO | WO 03/106447 | 12/2003 |
| WO | WO 2004/014872 | 2/2004 |
| WO | WO 2004/054986 | 7/2004 |
| WO | WO 2004/108691 | 12/2004 |
| WO | WO 2004/113314 | 12/2004 |
| WO | WO 2005/023779 | 3/2005 |
| WO | WO 2005/028450 | 3/2005 |
| WO | WO 2005/042522 | 5/2005 |
| WO | WO 2006/067456 | 6/2006 |
| WO | WO 2007/007119 | 1/2007 |

OTHER PUBLICATIONS

Barry et al. (1983) Alkylations En Absence De Solvant Organique. Effets D'Addition D'Oxydes Mineraux Et De Sels D'Ammonium-II, Tetradron 39(16):2673-2677.
Bennett et al. (1991) Methyl (3R)-3-Hydroxyhex-5-Enoate as A Precursor to Chiral Mevinic Acid Analogues, J. Chem. Soc. 1:133-140.
Bram et al. (1985) Anionic Activation by Solid-Liquid Phase Transfer Catalysis Without Solvent: An Improvement in Organic Synthesis, Israel J. Chem. 26:291-298.
Chevallett et al. (1993) Facile Synthesis of Tert-Butyl Ester of N-Protected Amino Acids With Tert-Butyl Bromide, Tetrahedron Lett. 34(46):7409-7412.
Chikara et al. (1993) Preparation of Optically Active 5,6-Epoxyhexanoic Acid Esters as Materials for Physiologically Active Substances, 6001 Chemical Abstracts, 118(11):101787x.
Crowther et al. (1971) Esterification of Hindered Alcohols: tert-Butyl p-Toluate, Organ. Synth. 51, 96, pp. 259-262.
Halpern (1997) Choosing a Phase-Transfer Catalyst, Phase-Transfer Communications, 3(1):1-16.
Inanaga et al. (1979) A Rapid Esterification by Means of Mixed Anhydride and its Application to Large-Ring Lactonization, Bull. Chem. Soc. Jpn., 52(7):1989-1993.
Mar. (1992) Advanced Organic Chemistry; Reactions, Mechanisms and Structure, p. 392.
Murakami et al. (1990) 2,4,6-Tripyridinio-1,3,5-Triazine Trichloride, a New and Mild Esterification Agent for Preparation of Penicillin Esters, Heterocycles, 31(11):2055-2064.
Murphy et al. (1970) Chemistry of Cephalosporin Antibiotics. XVIII. Synthesis of 7-Acyl-3-Methyl-2-Cephem-4-Carboxylic Acid Esters, J. Org. Chem. 35(7):2429-2430.
Rayle et al. (1999) Development of a Process for Triazine-Promoted Amidation of Carboxylic Acids, Org. Proc. Res. & Dev. 3:172-176.
Sakaki et al. (1991) Lipase-Catalyzed Asymmetric Synthesis of 6-(3-Chloro-2-Hydroxypropyl)-1,3-Dioxin-4-Ones and Their Conversion to Chiral 5,6-Epoxyhexanoates, Tetrahedron Asymmetry 2(5):343-346.
Takeda et al. (Oct. 1994) Dicarbonates: Convenient 4-Dimethylaminopyridine Catalyzed Esterification Reagents, Synthesis, pp. 1063-1066.
Thierry et al. (1998) 2-Phenyl Isopropyl and t-Butyl Trichloroacetimidates: Useful Reagents for Ester Preparation of N-Protected Amino Acids Under Neutral Conditions, Tetrahedron Lett. 39:1557-1560.
Watanabe et al. (1997) Synthesis and Biological Activity of Methanesulfonamide Pyrimidine-And N-Methanesulfonyl Pyrrole-Substituted 3,5-Dihydroxy-6-Heptenoates, A Novel Series of HMG-CoA Reductase Inhibitors, Bioorg. Med. Chem. 5(2):437-444.
Watanabe et al. (1999) ZD-4522 Hypolipidemic HMG-CoA Reductase Inhibitor, Drugs of the Future, 24(5):511-513.
Wessenfels et al. (1972) Substituierte 2-Formylmethylen-2H-1-Benzopyrane Aus β-Chlorvinylaldehyden, Z Chem. 12(7):263-265.
Ziegler et al. (1979) A Mild Method for the Esterification of Fatty Acids, Synth. Comm. 9(6):539-543.
Phase Transfer Catalysis, Principles, and Techniques (C.M. Starks; Academic Press, 1978), pp. 140-147.
March, Advanced Organic Chemistry: Reactions, Mechanisms, and Structure, 4th ed., John Wiley & Sons, Inc, p. 378 (1992).
Menges et al. "Oxidative Degradation of γ-Butyrolactons into 1,3-Diols via a Criegee Rearrangement of Peroxosulfonates. An Enantioselective Synthesis of Compactin Lactone and its Diastereomer" Synlett 12:901-905 (1993).
Morrison and Boyd "Alkaline hydrolysis of esters" Lehrbuch der Organischen Chemie, 2nd ed., Verlag Chemie, p. 739 (1978) (Translation enclosed).
Patel et al. "Enantioselective microbial reduction of 3,5-dioxo-6-(benzyloxy) hexanoic acid, ethyl ester" Enzyme Microb. Technol. 15: 1014-1021 (1993).
Peters et al. "Studies on the distribution and regulation of microbial keto ester reductases" Applied Microbiology Biotechnology 38: 334-340 (1992).
Presentation given at the 20th International Congress of Heterocyclic Chemistry in Palermo, Aug. 1st-5th, 2005.
Presentation given at the Gordon Conference on Heterocyclic Compounds, Salve Regina University, Newport, Rhode Island, Jul. 4-9, 2004.
Shao et al. "Asymmetric hydrogenation of 3,5-Dioxoesters catalyzed by Ru-binap complex: A short step asymmetric synthesis of 6-substituted 5,6-dihydro-2-pyrones" Tetrahedron 49(10):1997-2010 (1993).

* cited by examiner

PROCESS FOR THE PREPARATION OF DIHYDROXY ESTERS AND DERIVATIVES THEREOF

This application is a Divisional Application of U.S. application Ser. No. 12/178,424, filed Jul. 23, 2008 now U.S. Pat. No. 7,732,171, now allowed, which is a continuation application of U.S. application Ser. No. 11/412,047, filed Apr. 27, 2006, now U.S. Pat. No. 7,416,865, which is a continuation of U.S. application Ser. No. 10/275,092, filed Nov. 1, 2002, now U.S. Pat. No. 7,157,255, which is a U.S. National Phase Application of International Application No. PCT/GB01/01915, filed May 1, 2001, which claims the benefit of Great Britain Application No. 0011120.3, filed May 9, 2000, all of which are herein incorporated by reference in their entireties.

The present invention concerns a stereoselective process for the preparation of dihydroxy esters, and derivatives thereof.

According to a first aspect of the present invention, there is provided a process for the preparation of a compound of formula (1)

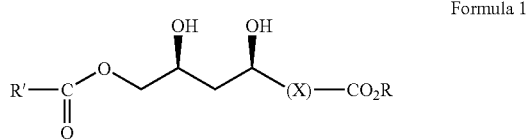

Formula 1 which comprises either a) the stereoselective reduction of a compound of formula (2)

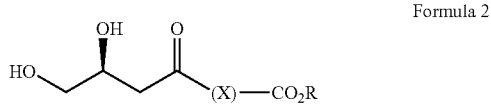

Formula 2 to produce a compound of formula (3), and

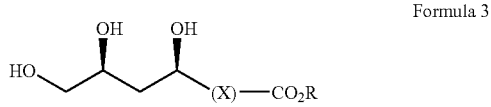

Formula 3 b) Esterification of the compound of formula (3) in the presence of a compound of formula R"—O—COR' and a lipase or hydrolase enzyme thereby to form the compound of formula (1); or c) Esterification of a compound of formula (2) in the presence of a compound of formula R"—O—COR' and a lipase or hydrolase enzyme thereby to form the compound of formula (4), and

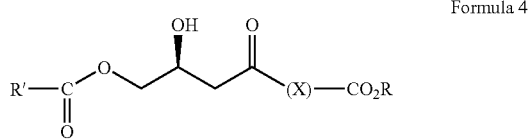

Formula 4 d) the stereoselective reduction of a compound of formula (4) to produce a compound of formula (1)

wherein

X represents an optionally substituted hydrocarbyl linking group

R and R" each independently represent an optionally substituted hydrocarbyl group, and R' represents an optionally substituted hydrocarbyl, preferably an optionally substituted alkyl group.

Hydrocarbyl groups represented by X, R, R' or R" may be substituted by one or more substituents, and may be persubstituted, for example perhalogenated. Examples of substituents include halo, especially fluoro and chloro, alkoxy, such as $C_{1-4}$ alkoxy, and oxo.

Preferably, X represents a group of formula —$(CH_2)_n$— where n is from 1 to 4, and most preferably X represents a group of formula —$CH_2$—.

R" may be an alkyl group, such as a $C_{1-6}$ alkyl group, or an alkylcarbonyl group, such as a $C_{1-6}$ alkylcarbonyl group, for example a $CH_3(C=O)$— or $CF_3(C=O)$— group. R" is most preferably a vinyl or isopropenyl group.

R preferably represents a $C_{1-6}$ alkyl group, which may be linear or branched, and may be substituted by one or more substituents. Most preferably, R represents a t-butyl group.

R' may represent a substituted alkyl, often $C_{1-6}$ alkyl group, such as a $CF_3$— or $CF_3CH_2$— group, but is preferably an unsubstituted $C_{1-6}$ alkyl group, and most especially a methyl group.

The stereoselective reduction of the compounds of formulae (2) or (4) preferably employ chemical or microbial reduction methods, such as hydrogenation, transfer hydrogenation, metal hydride reduction or dehydrogenases. Examples of a suitable hydrogenation process such as that described in Helv. Chim. Acta 69, 803, 1986 (incorporated herein by reference) include the use of between 0.01 and 10% (w/w) of catalysts such as platinum, palladium or rhodium on heterogeneous supports such as carbon, alumina, silica using molecular hydrogen at between 1 and 10 bar in a solvent such as methanol, ethanol, t-butanol, dimethylformamide, t-butylmethylether, toluene or hexane. Alternatively homogenous hydrogenation catalysts such as those described in EP0583171 (incorporated herein by reference) may be used.

Examples of suitable chemical transfer hydrogenation processes include those described in Zassinovich, Mestroni and Gladiali, Chem. Rev. 1992, 92, 1051 (incorporated herein by reference) or by Fuji et al in J. Am. Chem. Soc. 118, 2521, 1996 (incorporated herein by reference). Preferred chemical transfer hydrogenation processes employ chiral ligated complexes of transition metals, such as ruthenium or rhodium, especially chiral diamine-ligated neutral aromatic ruthenium complexes. Preferably, such a chemical transfer hydrogenation employs an acid, especially a formate salt such as triethylammonium formate, as the hydrogen source.

Metal hydride reagents such as those described in Tet. 1993, 1997, Tet. Asymm. 1990, 1, 307, (incorporated herein by reference), or J. Am. Chem. Soc. 1998, 110, 3560 (incorporated herein by reference) can be used.

Examples of suitable microbial reductions include contacting the compound of formula (2) or (4) with an organism possessing the properties of a microorganism selected from *Beauveria* preferably *Beauveria bassiana*, *Pichia* preferably *Pichia angusta* or *Pichia pastoris, trehalophila, haplophila* or *membranefaciens*. *Candida* preferably *Candida humicola, solani, guillermondii, diddenssiae* or *friedrichii*. *Kluyveromyces* preferably *Kluyveromyces drosophilarum*, or *Toru-*

*laspora* preferably *Torulaspora hansenii*. The reduction may be achieved by contacting the compounds of formulae (2) or (4) with an enzyme extracted from the foregoing microorganisms. Most preferably, the compounds of formulae (2) or (4) are contacted with a microorganism selected from *Pichia angusta, Pichia pastoris, Candida guillermondii, Saccharomyces carlsbergensis, Pichia trehalophila, Kluyveromyces drosopliarum* and *Torulospora hansenii*, or an extract from the foregoing organisms.

The invention preferably comprises producing a compound of formula (3) by selectively reducing a compound of formulae (2) using whole cells of or extracts from the aforementioned microorganisms, preferably *Pichia angusta, Pichia pastoris, Candida guillermondii, Saccharomyces carlsbergensis, Pichia trehalophila, Kluyveromyces drosopliarum* and *Torulospora hansenii*.

The invention is most preferably carried out using whole cells of the organisms as this avoids the need to separate the desired enzyme and provides co-factors for the reaction.

Any of the above species may be used but in many embodiments, it has been found that high conversions and high selectivity can be achieved by the use of the enzyme or whole cells of *Pichia angusta*.

In general a co-factor, normally NAD(P)H (nicotinamide adenine dinucleotide or nicotinamide adenine dinucleotide phosphate) and a system for re-generating the co-factor, for example glucose and glucose dehydrogenase, are used with the enzymes to drive the reaction. As suitable co-factors and reduction mechanisms are present in the whole cells it is preferred to use the whole cells in a nutrient medium which preferably contains a suitable carbon source, which may include one or more of the following: a sugar, e.g. maltose, sucrose or preferably glucose, a polyol e.g. glycerol or sorbitol, citric acid, or a lower alcohol, for example methanol or ethanol.

If whole cells are intended to grow during the reaction nitrogen and phosphorus sources and trace elements should be present in the medium. These may be those normally used in culturing the organism.

The process may be carried out by adding a compound of formula (2) or (4) to a culture of the growing organism in a medium capable of supporting growth or to a suspension of the live cells in a medium which preferably contains a carbon source but which lacks one or more nutrients necessary for growth. Dead cells may also be used providing the necessary enzymes and co-factors are present; if necessary they may be added to the dead cells.

If desired the cells may be immobilised on a support which is contacted with compound of formula (2) or (4) preferably in the presence of a suitable carbon source as previously described.

The pH is suitably 3.5 to 9, for example 4 to 9, preferably at most 6.5 and more preferably at most 5.5. Very suitably a pH of 4 to 5 is used. The process may suitably be carried out at a temperature of 10 to 50° C., preferably 20 to 40° C. and more preferably 25 to 35° C. It is preferred to operate under aerobic conditions if live whole cells of the aforesaid organisms are present. An aeration rate equivalent to 0.01 to 1.0 volumes of air measured at standard temperature and pressure per volume of the culture medium per minute is suitably employed at the aforesaid conditions of pH and temperature but it will be appreciated that considerable variation is possible. Similar pH, temperature and aeration conditions may be used during growth of the organisms if this is carried out separately from the process.

Purified enzymes may be isolated by known means suitably by centrifuging a suspension of disintegrated cells and separating a clear solution from debris, separating the desired enzyme from the solution for example by ion exchange chromatography suitably with elution from the column with liquid of increasing ionic strength and/or by selective precipitation by the addition of an ionic material, for example ammonium sulphate. Such operations may be repeated if desired to enhance purity.

The microbial reduction of compounds of formula (2) or (4) is particularly preferred, and this process forms a second aspect of the present invention.

In the esterification of compounds of formula (2) or (3) it is preferred to transesterify with another ester, which is present in at least mole equivalence with respect to the alcohol and is suitably a vinyl ester (as the by-product, acetaldehyde is not involved in a back-reaction). Alternatively an anhydride such as acetic anhydride or trifluoroacetic anhydride, or an ester such as ethylacetate or a fluorinated ester such as trifluoroethylacetate may be used. It is preferred that the regiospecific esterification reaction be carried out in an organic solvent containing less than 1% (w/w) water such as acetonitrile, ethylacetate, tetrahydrofuran, tert-butylmethylether, toluene, butanone, pentanone or hexanone at a temperature of preferably 20 to 75° C., more preferably 25 to 50° C. The esters are preferably esters of lower alkanoic acids having 2 to 8 carbon atoms, or substituted derivatives thereof. Optionally an inert atmosphere may be employed, for example a flow of nitrogen may be passed through the solution.

The enzymes may be provided as such or as whole cells comprising them. It is preferred that they be immobilised so as to facilitate their separation from the product and, if desired, re-use.

Preferred enzymes include lipases such as Porcine pancreatic lipase. *Candida cylindracea* lipase. *Pseudomonas fluorescens* lipase. *Candida antarctica* fraction B such as that available under the trade mark Chirazyme L2, those from *Humicola lanuginosa* for example that sold under the Trade Mark Lipolase or those from *Pseudomonas* for example that sold under the Trade Mark SAM II and more preferably those from *Candida antarctica*, for example that sold under the Trade Mark Chirazyme.

Compounds of formula (1) wherein R' is $CH_3$, R is optionally substituted hydrocarbyl. X is $—(CH_2)_n—$ and n is 1 to 4 form a third aspect of the present invention. Preferably. R is t-butyl and most preferably, X is $—CH_2—$.

Compounds of formula (1) are useful intermediates for the preparation of pharmaceutical compounds. Commonly, they are reacted with a protecting group for 1,3-dihydroxy moieties such as 2,2-dimethoxypropane to form an acetonide as described in Synthesis 1998, 1713. The group R'—(C=O)— may then be selectively removed by treatment with weakly basic alcoholic solution eg $K_2CO_3$ solution as described in U.S. Pat. No. 5,278,313 or a lipase either in aqueous solution, or in organic solution containing sufficient water to support hydrolysis, to form a compound of formula (5):

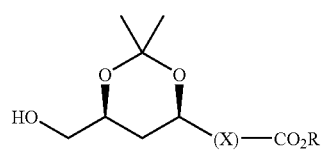

Formula 5

EXAMPLE 1

Preparation of (3R,5S) t-butyl 3,5,6-trihydroxyhexanoate

To a stirred 250 ml round bottom flask 20 ml acetonitrile, 0.405 g (0.662 mmoles) of di-mu-chlorobis[(p-cymene)chlororuthenium (II)], and 0.492 g (1.34 mmoles) (1S,2S)-(+)-N-(4-toluenesulfonyl)-1,2-diphenylethylenediamine were charged. The solution was de-oxygenated by sparging with nitrogen and thereafter maintaining a trickle. A de-oxygenated solution of 26 g (0.119 mol) optically pure (5S) t-butyl 3-keto-5,6-dihydroxyhexanoate in 15 ml acetonitrile was charged to the reaction vessel and the solution stirred at ambient temperature for 20 minutes, 65 ml of a 5:2 (mol/mol) mixture of distilled formic acid and triethylamine were then added over a period of 10 minutes and the reaction mixture stirred at ambient temperature for 48 hours. To this solution 80 ml dichloromethane and 120 ml saturated sodium bicarbonate were slowly added. 70 g ammonium chloride was charged to the aqueous layer and the organic layer separated. The aqueous layer was washed thrice more with 90 ml ethylacetate, the organic fractions combined, dried over sodium sulfate and the solvent removed to give 21.1 g of a crude oil containing mainly (3R,5S) t-butyl 3,5,6-trihydroxyhexanoate. The ratio of diastereomers was determined by $^{13}$CNMR to be 5.2:1 (3R:5S): (3S:5S). The material was used crude in the next reaction but could be purified by column chromatography.

Preparation of (3R,5S) t-butyl 6-acetoxy-3,5-dihydroxyhexanoate

To a stirred 1 l round bottom flask 700 ml tetrahydrofuran and 70.7 g (0.32 mol) of (3R,5S) t-butyl 3,5,6-trihydroxyhexanoate, 41 ml (0.46 mol) vinylacetate and 6.3 g of the supported lipase Chirazyme L2™ were charged. After 3 hours stirring at ambient temperature the lipase was removed by screening and the volatiles removed by distillation under vacuum. The mass of crude oil was 78.7 g and the major component was determined to be (3R,5S) t-butyl 6-acetoxy-3,5-dihydroxyhexanoate. This material was used directly in the next stage.

Preparation of (4R,6S)-6-[(acetyloxy)methyl]-2,2-dimethyl-1,3-dioxane-4-acetic acid, 1,1-dimethylethylester To a stirred 1 litre round bottom flask 78.7 g (3R,5S) t-butyl 6-acetoxy-3,5-dihydroxyhexanoate, 800 ml of 2,2-dimethoxypropane and 5.7 g p-toluenesulfonic acid were charged. After 35 minutes thee reaction mass was concentrated to half its volume and 300 ml of dichloromethane and 300 ml of 1M sodiumbicarbonate added. The organic layer was separated and the aqueous layer washed thrice more with 150 ml ethylacetate. The organic fractions were combined, dried over sodium sulfate and the volatiles removed by distillation under vacuum. 92 g of a crude oil was obtained. This was purified first by passing through a short column of flash silica and eluting with hexane and then hexane:ethylacetate 85:15 (v/v), and then crystallising the material 3 times from hexane to give 22.17 g (4R,6S)-6-[(acetyloxy)methyl]-2,2-dimethyl-1,3-dioxane-4-acetic acid, 1,1-dimethylethylester which by chiral GC was determined to be 99.9% de.

Preparation of (4R,6S)-6-(hydroxymethyl]-2,2-dimethyl-1,3-dioxane-4-acetic acid, 1,1-dimethylethylester To a 500 ml stirred round bottom flask 22.17 g of (4R,6S)-6-[(acetyloxy)methyl]-2,2-dimethyl-1,3-dioxane-4-acetic acid, 1,1-dimethylethylester, 250 ml methanol and 5.05 g crushed potassium carbonate were charged. The reaction was stirred for 35 minutes until the hydrolysis was complete, then the potassium carbonate was removed by screening, the reaction mass concentrated and 150 ml 5% (w/w) brine and 150 ml toluene added. The organic layer was separated and the aqueous washed twice more with 250 ml toluene. The organic layers were combined, washed three times with 15% (w/w) brine and the solvent removed by vacuum distillation to give 17.78 g of clear oil, which was determined to be >99% (4R,6S)-6-(hydroxymethyl)-2,2-dimethyl-1,3-dioxane-4-acetic acid, 1,1-dimethylethylester.

EXAMPLE 2

Preparation of (5S) tert-butyl 6-acetoxy-5-hydroxy-3-ketohexanoate

To a stirred 250 ml round bottom flask were charged 2.32 g (0.0106 moles) (5S) tert-butyl 5,6-dihydroxy-3-ketohexanoate, 40 ml tetrahydrofuran, 0.98 ml (0.0106 moles) vinyl acetate and 0.22 g of the supported lipase Chirazyme L2™. After 20 minutes the lipase was removed by screening and the volatiles removed by distillation under vacuum, to give 2.96 g of a crude oil that was characterised by NMR as (5S) tert-butyl 6-acetoxy-5-hydroxy-3-ketohexanoate.

EXAMPLE 3

Preparation of (3R,5S) t-butyl 3,5,6-trihydroxyhexanoate

*Pichia angusta* NCYC R230 (deposited under the provisions of the Budapest Treaty on May 18$^{th}$, 1995) was grown in a Braun Biostat Q multi-fermenter system in the following medium (per litre): glucose 40 g; MgSO$_4$, 1.2 g; K$_2$SO$_4$, 0.21 g; KH$_2$PO$_4$, 0.69 g; H$_3$PO$_4$ (concentrated), 1 ml; yeast extract (Oxoid), 2 g; FeSO$_4$.7H$_2$O, 0.05 g; antifoam (EEA 142 Foammaster), trace elements solution, 1 ml (this solution contained per litre CuSO$_4$.5H$_2$O, 0.02; MnSO$_4$.4H$_2$O, 0.1 g; ZnSO$_4$.7H$_2$O, 0.1 g; CaCO$_3$, 1.8 g.

Each of 4 fermenters were charged with 250 ml of medium and sterilised by autoclaving. The pH was adjusted to 4.5 using 7 molar ammonium hydroxide solution, the temperature was set to 28° C., the air flow set at 300 ml/minute and the agitator speed set to 1200 rpm. Fermenters were inoculated with cells taken from agar plates (2% agar) comprising the same medium as described above except that the glucose concentration was 20 g/litre. Following 22 hours growth in the fermenters the bioreduction reaction was started by the addition of (5S) t-butyl 3-keto-5,6-dihydroxyhexanoate; two of the fermenters were charged with 3.75 ml each and the other two charged with 5 ml each.

The reaction was continued for a further 78 hours until 100% conversion of substrate. During this period the culture was fed with a 50% solution of glucose at a rate of 1-3 grams glucose/litre culture/hour to maintain cell viability and provide a source of reducing power. Reactions were terminated by removal of the cells by centrifugation. To the recovered cell-free supernatant was added sodium chloride to a final concentration of 20% w/v and the mixture extracted three times with an equal volume of acetonitrile. The pooled acetonitrile extracts were dried with anhydrous sodium sulfate and the solvent removed under reduced pressure in a rotary evaporator (water bath temperature 45° C.) to yield a viscous pale yellow oil. The identity of the product from each reaction was confirmed as (3R,5S) t-butyl 3,5,6-trihydroxyhexanoate and the diastereomeric excess of each of the samples is given in the table below.

| experiment | diastereomeric excess (%) |
|---|---|
| 1 | 99.6 |
| 2 | 99.6 |
| 3 | 99.4 |
| 4 | 99.6 |

EXAMPLE 4

Preparation of (3R,5S) t-butyl 3,5,6-trihydroxyhexanoate

*Pichia angusta* NCYC R320 (deposited under the provisions of the Budapest Treaty on May 18, 1995) was grown in a Braun Biostat Q multi-fermenter system in the following medium (containing, per litre): glucose, 20 g; ammonium sulfate, 10 g; Yeast extract (Oxoid), 2 g; MgSO$_4$.7H$_2$O, 1.2 g; KH$_2$PO$_4$, 0.69 g; K$_2$SO$_4$, 0.21 g; FeSO$_4$.7H$_2$O, 0.05 g; H$_3$PO$_4$ (concentrated), 1 ml; EEA 142 "foammaster" antifoam, 0.5 ml; trace elements solution, 1 ml (this solution contained per litre Ca(CH$_3$CO$_2$)$_2$, 2.85 g; ZnSO$_4$.7H$_2$O, 0.1 g; MnSO$_4$.H$_2$O 0.075 g CuSO$_4$.5H$_2$O, 0.02 g; sulphuric acid (concentrated), 1 ml).

One fermenter was charged with 250 ml medium and sterilised by autoclaving. The pH was adjusted to 5.0 using 2 molar sodium hydroxide solution. The temperature was set to 28° C., the air flow was set to 250 ml minute$^{-1}$ and the agitator speed set to 1200 rpm. The fermenter was inoculated with 2.5 ml of a suspension of cells in sterile deionised water prepared from an agar plate of *Pichia angusta* NCYC R320. Following 17 hours growth the bioreduction was started by the addition of 6.36 g 5(S) t-butyl 3-keto-5,6-dihydroxyhexanoate as an aqueous solution. At the same time a glucose feed to the fermenter was started at a rate of 2 g glucose L$^{-1}$ h$^{-1}$.

The reaction was continued for a further 78 hours at which point 96% conversion of the substrate had been achieved. Starting material and product were detected by HPLC (Hichrom S5 CN-250A column, temperature 35° C., mobile phase: aqueous TFA (0.1%): acetonitrile 95:5, flow rate 1 ml min$^{-1}$, injection volume 5 ml, refractive index detector).

The reaction was terminated by the removal of cells by centrifuging at 4000×g for 20 minutes. The pH of the recovered cell-free supernatant was adjusted to 7.5 using 2M NaOH. MgSO$_4$.1.6H$_2$O (15% w/v based on anhydrous) was dissolved in the cell-free supernatant and the resulting solution was extracted twice with an equal volume of 2-pentanone. The solvent phases were collected and the solvent removed under reduced pressure in a rotary evaporator at 45° C. yielding an orange viscous oil. This was re-dissolved in 50 ml dry, distilled 2-pentanone and again the solvent was removed by rotary evaporation to afford t-butyl 3,5,6-trihydroxyhexanoate (5.08 g, 80% isolated yield). Diastereomeric excess was determined as follows; a sample of t-butyl 3,5,6-trihydroxyhexanoate (30 mg) was derivatised by reaction for at least 10 minutes at room temperature in an excess of trifluoroacetic anhydride, excess anhydride was removed under a stream of dry nitrogen and the residual oil diluted with dichloromethane (1 ml). The sample was analysed using a Chiralcel Dex CB column (25 metre) at a temperature of 140° C. (isothermal). The diastereomers eluted at 14.4 minutes (3R,5S diastereomer) and 15.7 minutes (3S,5S diastereomer). The diastereomeric excess of the sample was found by this method to be 99.7%.

The invention claimed is:

1. A process for the preparation of a compound of formula (4)

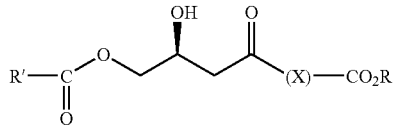

Formula 4 which comprises esterification of a compound of formula (2)

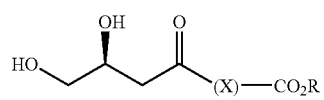

Formula 2 in the presence of a compound of formula R"–O—COR' and a lipase or hydrolase enzyme thereby to form the compound of formula (4);
wherein
X represents an optionally substituted hydrocarbyl linking group;
R and R" each independently represent an optionally substituted hydrocarbyl group; and
R' represents an optionally substituted hydrocarbyl group.

2. The process according to claim 1 wherein X is —CH$_2$—.

3. The process according to claim 1 wherein R" is a vinyl or isopropenyl group.

4. The process according to claim 1 wherein R' represents a substituted or unsubstituted C$_{1-6}$ alkyl group.

5. The process according to claim 1 wherein R' is CH$_3$, R is t-butyl and X is —CH$_2$—.

6. The process according to claim 1 wherein the enzyme is selected from the group consisting of *Porcine pancreatic* lipase, *Candida cylindracea* lipase, *Pseudomonas fluorescens* lipase, *Candida antarctica* fraction B and lipase from *Humicola lanuginosa*.

7. The process according to claim 1 wherein the compound of formula R"–O—COR' is vinyl acetate.

* * * * *